United States Patent
Qutub

(10) Patent No.: US 9,084,613 B2
(45) Date of Patent: Jul. 21, 2015

(54) METHOD AND APPARATUS FOR DETERMINING AND GUIDING THE TOOLPATH OF AN ORTHOPEDIC SURGICAL ROBOT

(76) Inventor: Motaz Qutub, Allen, TX (US)

(*) Notice: Subject to any disclaimer, the term of this patent is extended or adjusted under 35 U.S.C. 154(b) by 0 days.

(21) Appl. No.: 13/529,562

(22) Filed: Jun. 21, 2012

(65) Prior Publication Data
US 2013/0035696 A1    Feb. 7, 2013

Related U.S. Application Data

(60) Provisional application No. 61/499,500, filed on Jun. 21, 2011.

(51) Int. Cl.
| | |
|---|---|
| *A61B 19/00* | (2006.01) |
| *A61B 17/16* | (2006.01) |
| *A61B 17/32* | (2006.01) |
| *A61B 18/20* | (2006.01) |

(52) U.S. Cl.
CPC ............ *A61B 17/16* (2013.01); *A61B 19/2203* (2013.01); *A61B 19/50* (2013.01); *A61B 17/1626* (2013.01); *A61B 17/32002* (2013.01); *A61B 18/20* (2013.01); *A61B 19/30* (2013.01); *A61B 19/5244* (2013.01); *A61B 2017/1602* (2013.01); *A61B 2019/5291* (2013.01)

(58) Field of Classification Search
CPC ............................ A61B 19/50; A61B 19/2203
USPC .......................................................... 606/79
See application file for complete search history.

(56) References Cited

U.S. PATENT DOCUMENTS

| | | | |
|---|---|---|---|
| 6,770,078 B2* | 8/2004 | Bonutti | 606/88 |
| 8,679,125 B2* | 3/2014 | Smith et al. | 606/81 |

* cited by examiner

*Primary Examiner* — Andrew Yang
(74) *Attorney, Agent, or Firm* — Pandiscio & Pandiscio

(57) ABSTRACT

A surgical robot system for cutting bone, the surgical robot system comprising:
a surgical robot having an end effector;
a cutter attached to the end effector;
position determining means for determining the position of a bone which is to be cut vis-à-vis the surgical robot;
pre-plan means for storing a pre-planned cut of the bone and instructing the surgical robot to cut bone in accordance with the same;
a display for displaying the pre-planned cut of the bone; and
input means for enabling a user to deactivate the pre-plan means and to enable manual control of the cutter by the user.

19 Claims, 5 Drawing Sheets

THE ROBODOC SURGICAL ASSISTANT SYSTEM

THE ROBODOC SURGICAL ASSISTANT SYSTEM

THE CAMERA ATTACHMENT TO THE ROBOT END EFFECTOR

THE USER INTERFACE SCREEN

THE JOYSTICK COMMAND AND THE ACTUAL MOVEMENT OF THE ROBOT

THE FORCE SENSOR COMMAND AND THE ACTUAL MOVEMENT OF ROBOT

METHOD AND APPARATUS FOR DETERMINING AND GUIDING THE TOOLPATH OF AN ORTHOPEDIC SURGICAL ROBOT

REFERENCE TO PENDING PRIOR PATENT APPLICATION

This patent application claims benefit of prior U.S. Provisional Patent Application Ser. No. 61/499,500, filed Jun. 21, 2011 by Motaz Qutub for METHOD AND APPARATUS TO MAKE AND GUIDE THE TOOLPATH OF AN ORTHOPEDIC SURGICAL ROBOT, which patent application is hereby incorporated herein by reference.

FIELD OF THE INVENTION

This invention relates to methods and apparatus for controlling robots in general, and more particularly to methods and apparatus for intraoperative control of an orthopedic surgical robot which is equipped with a high speed cutting tool to machine bone in a precise manner.

BACKGROUND OF THE INVENTION

The use of high speed cutting tools such as rotary burrs and oscillating saws significantly reduces operating time and surgeon labor in orthopedic surgical procedures. Such power tools enable significantly faster cutting of bone during a surgical procedure, but when they are used manually, the accuracy of the cutting may not always be satisfactory.

Recently, surgical robots have become available which can control the power cutting tools used in orthopedic surgical procedures so as to provide superior accuracy in cutting bone. With orthopedic surgical robots, the key factor in determining the safety, accuracy and efficiency of the cutting performed by the orthopedic surgical robot is control of the toolpath during the surgical procedure.

With the Robodoc® surgical assistant system (Curexo Technology Corp., Fremont, Calif., USA), the surgical robot is equipped with a high speed rotating burr. A predefined cut path, selected for a specific implant, is loaded into the surgical robot, and the system then automatically cuts bone according to the pre-defined cut path, i.e., the surgical robot automatically cuts bone to the programmed positions.

With the TGS™ surgical robot system (Mako Surgical Corp., Fort Lauderdale, Fla., USA), the surgical robot is equipped with a high speed rotating burr. A predefined cut volume, selected for a specific implant, is loaded into the surgical robot. Then, while the surgical robot limits the location of the burr to within the predefined cut volume, the surgeon manually moves the burr into the bone so as to cut the bone out to the limit of the programmed positions.

The purpose of the present invention is to improve on the foregoing approaches, by providing a novel method and apparatus for determining and guiding the toolpath of an orthopedic surgical robot so as to enhance the safety, accuracy and efficiency of the cutting.

SUMMARY OF THE INVENTION

The present invention provides a novel method and apparatus for determining and guiding the toolpath of an orthopedic surgical robot so as to enhance the safety, accuracy and efficiency of the cutting.

In one preferred form of the invention, there is provided a surgical robot system for cutting bone, the surgical robot system comprising:
  a surgical robot having an end effector;
  a cutter attached to the end effector;
  position determining means for determining the position of a bone which is to be cut vis-à-vis the surgical robot;
  pre-plan means for storing a pre-planned cut of the bone and instructing the surgical robot to cut bone in accordance with the same;
  a display for displaying the pre-planned cut of the bone; and
  input means for enabling a user to deactivate the pre-plan means and to enable manual control of the cutter by the user.

In one preferred form of the invention, the surgical robot system further comprises a video camera attached to the surgical robot for capturing an image of the working portion of the cutter, and the display displays the pre-planned cut of the bone and the image captured by the video camera.

In another preferred form of the invention, there is provided a method for cutting bone, the method comprising:
  providing pre-planned cutting instructions to a surgical robot;
  automatically cutting bone with the surgical robot using the pre-planned cutting instructions;
  enabling a surgeon to assert manual control of the surgical robot at any time while the surgical robot is automatically cutting bone according to the pre-planned cutting instructions, by: (i) interrupting automatic operation of the surgical robot; (ii) establishing manual cutting boundaries to limit cutting by the surgical robot while the surgical robot is under the manual control of the surgeon; and (iii) manually controlling cutting by the surgical robot using input controls on the surgical robot.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
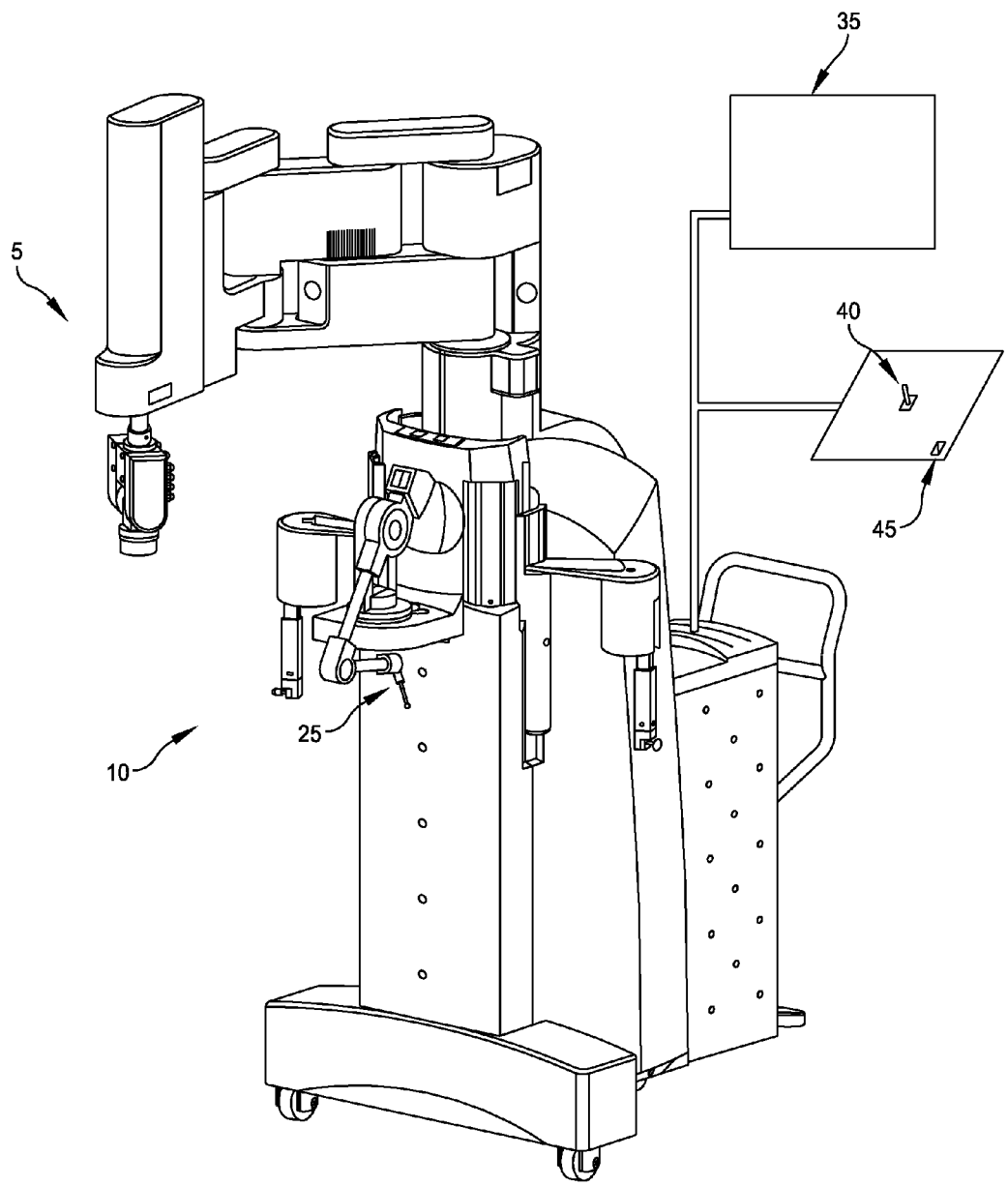
FIGS. 1-3 are schematic views showing a novel surgical robot system formed in accordance with the present invention.

As noted above, the Robodoc® surgical assistant system (Curexo Technology Corp., Fremont, Calif., USA) is an autonomous surgical robot that receives its cutting instructions and input data from a pre-planned file, and then utilizes that pre-planned file to automatically cut bone according to the pre-planned file, i.e., the surgical robot automatically cuts bone to the programmed positions. This pre-planned file is generally created by a surgeon using Orthodoc® pre-operative surgical planning software (Curexo Technology Corp., Fremont, Calif., USA) to plan the appropriate position of an implant relative to the patient's bone using the patient's CT scan data. More particularly, with this system, the surgeon uses the patient's CT scan data to derive a virtual model of the patient's bone, then appropriately positions a virtual model of the desired implant relative to the virtual model of the patient's bone, and then uses this virtual model positioning to determine how the patient's bone should be cut to receive the desired implant. The results are output in the form of the aforementioned pre-planned file, which is then used by the surgical robot to automatically cut the bone.

Unfortunately, during the actual surgery, in some cases the surgeon may wish to modify the pre-planned cutting, e.g., for the following reasons. First, inasmuch as the "off-the-shelf" implant is not patient-specific, the patient's bone may not exactly match the implant shape and there might be cutting which is not necessary. Second, if soft tissue is located next to the bone, and if the predefined tool path moves the cutter too close to the soft tissue, then the surgeon may not wish the cut that area of the bone with the high-speed rotary burr, and instead may wish to finish off the cut manually, after the robotic cutting. Third, if surgical access to the bone is limited, then the surgeon may wish to change the angle of the cutting tool during cutting, i.e., from the predefined tool axis to another tool axis preferred by the surgeon.

In this case, where the surgeon wishes to make a modification to the pre-planned cut during the actual surgical procedure, the surgeon has the option of either (i) allowing the Robodoc® surgical robot to finish the pre-planned cut, and thereafter modifying the robot-effected cut with further manual cutting, or (ii) aborting the ongoing Robodoc® procedure and then switching to manual cutting tools so as to modify the cut. Either of these approaches will, of course, defeat the purpose of utilizing a Robodoc® operation in the first place.

There are two possible solutions to this problem: one solution is to allow the surgeon to modify the original Orthodoc® planning file during the actual surgical procedure so as to implement the surgeon's desired changes, and the other solution is to allow the surgeon to take over control the Robodoc® surgical robot during the actual surgery, but only under strict control guidance so as to ensure the safety and accuracy of the cutting.

The present invention is directed to this latter approach, i.e., to allowing the surgeon to take over control of the Robodoc® surgical robot during the actual surgery so as to allow modification of the pre-planned cut according to the surgeon's professional judgment, but only under strict control guidance so as to ensure the safety and accuracy of the cutting.

Thus, with the present invention, the surgeon is able to move the robot tip (where the cutter is disposed) to specific locations on the bone which the surgeon wishes to remove (and which were not in the pre-programmed file previously loaded into the surgical robot). To this end, the present invention provides the surgical robot with a workstation which includes a display where the surgeon can simultaneously see the patient's CT scan, the planned cut against the CT scan, and the current position of the actual cutting tool vis-à-vis the actual bone. Before cutting can commence, the surgeon is required to set some boundaries for the manual cutting, and the workstation display also shows these manual cutting boundaries on the screen, preferably using a different color to distinguish the manual cutting boundaries from the pre-planned cut. These manual cutting boundaries include, but are not limited to, the maximum depth of the manual cutting (i.e., movement along the Z axis), as well as the maximum longitudinal and lateral movements of the manual cutting (i.e., movement along the X and Y axes). The surgeon can then make the manual cut by physical command (e.g., under joystick control) or by computer command (e.g., by selecting a predetermined manual cut from a drop-down menu of manual cuts, e.g., "cut a trough" of diameter A, length B, at depth C). A video camera mounted on the robot arm provides the surgeon with a visual image of the actual cutting tool vis-à-vis the actual bone so as to assist the surgeon in the decision-making, with the CT image on the workstation display being synchronized with the camera image on the workstation display so that the surgeon looks at both images from the same angle of view.

The actual feed rate of cutting is controlled by the software.

Where the surgeon is to operate the cutter under joystick control, the joystick preferably has a button to enable activation of joystick control—when this button is pushed, the end effector of the surgical robot (which carries the cutter) follows the motion of the joystick as operated by the surgeon, but when this button is not pushed, the joystick is deactivated.

Preferably another button is provided on the workstation which allows the surgeon to turn the cutter on or off.

Preferably, the system monitors force feedback on the cutter, and this information is displayed to the surgeon on the workstation display. The surgical robot system is preferably configured so that it will stop cutting if the force feedback exceeds a pre-set force limit.

Figure 2:
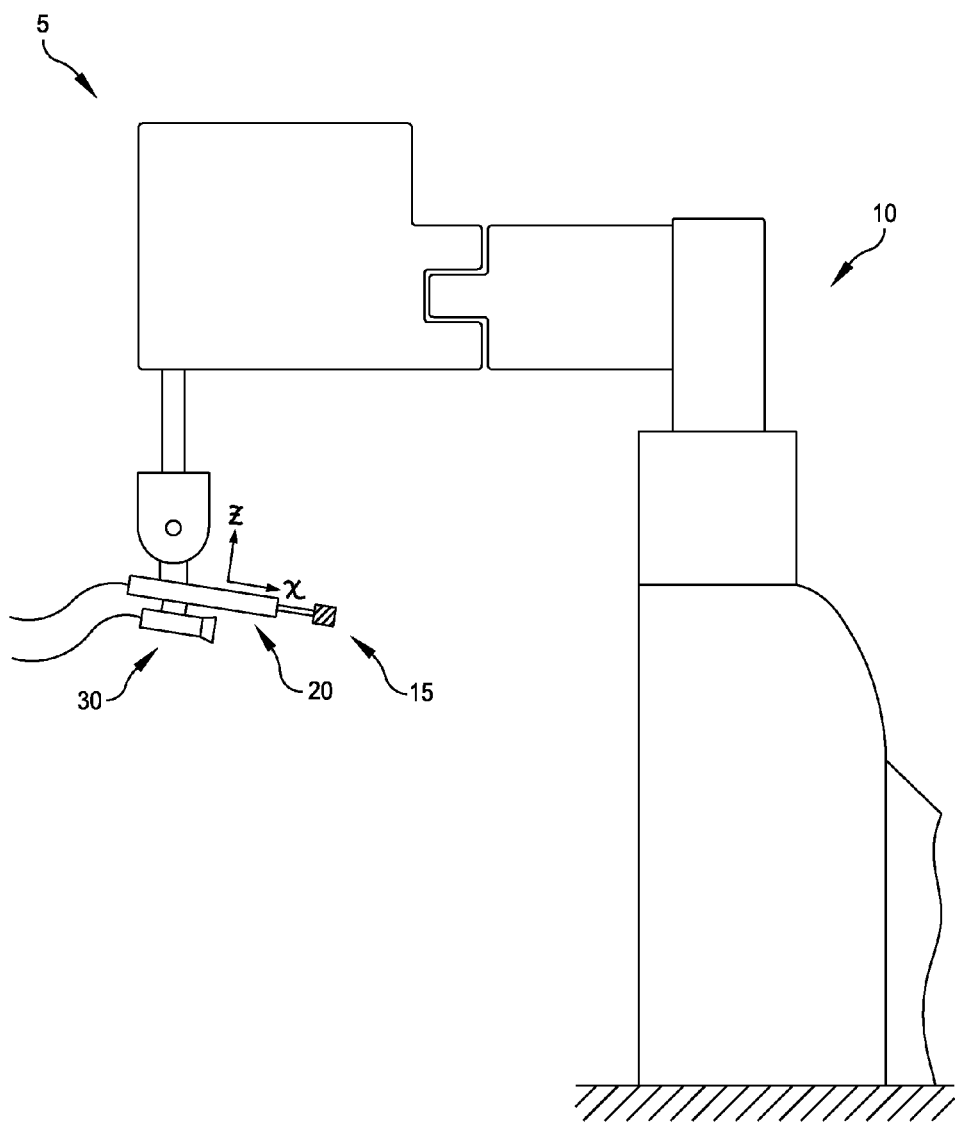
Figure 3:
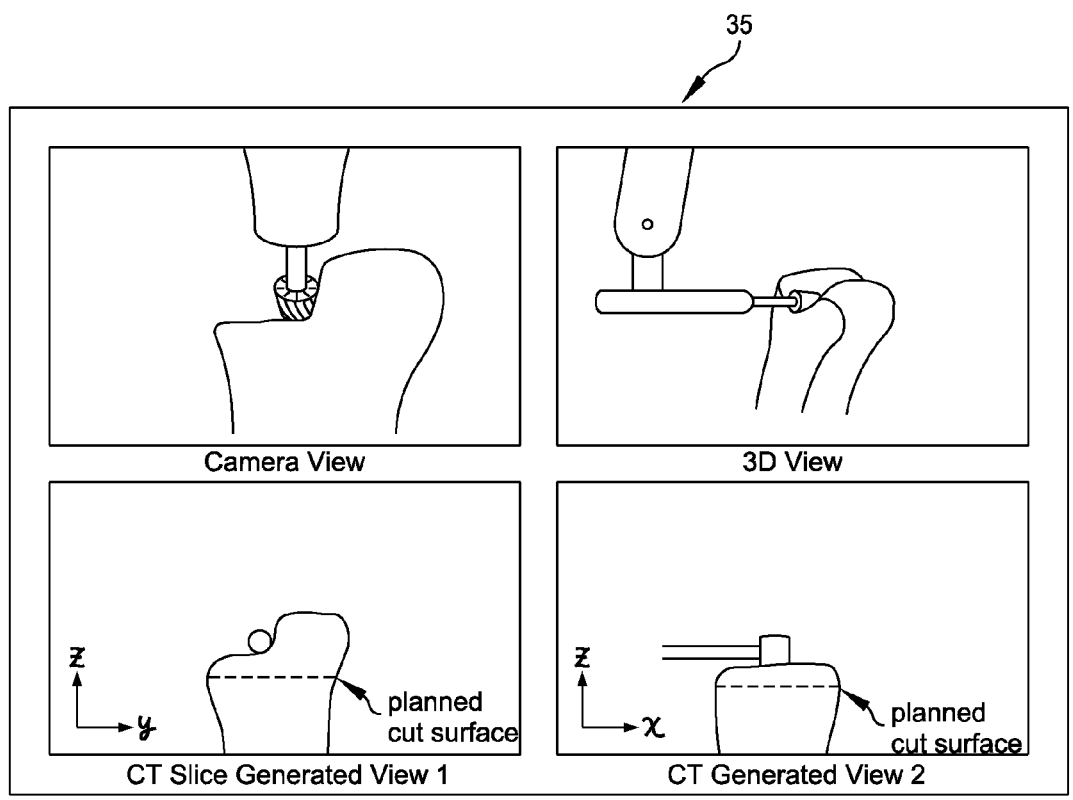

Looking now at FIG. 1-3, there is shown a novel surgical robot system 5 formed in accordance with the present invention. Novel surgical robot system 5 generally comprises a surgical robot 10 (e.g., a 5-axis surgical robot) which is equipped with high speed milling cutter 15 at the robot end effector 20, and a digitizer 25 which can digitize a plurality of points on the surface of a bone which is to be cut. By way of example but not limitation, surgical robot 10 may comprise the Robodoc® surgical assistant system (Curexo Technology Corp., Fremont, Calif., USA) appropriately modified (e.g., with appropriate software and hardware changes) in accordance with the present invention. In accordance with the present invention, novel surgical robot system 5 also comprises a video camera 30 attached to the robot end effector 20 which shows the working portion of the milling cutter 15, and a display 35 for displaying to the surgeon the aforementioned images (e.g., the patient's CT scan, the planned cut against the CT scan, and the current position of the actual cutting tool vis-à-vis the actual bone), and for displaying other information to the surgeon. Novel surgical robot system 5 preferably also comprises a joystick 40 for permitting the surgeon to take manual control of surgical robot 10 via physical command, and a cutter on/off switch 45. Novel surgical robot system 5 also comprises appropriate computer software which will be apparent to those skilled in the art in view of the present disclosure for enabling operation of novel surgical robot system 5 in accordance with the present invention.

In one preferred form of the invention, the novel surgical robot system 5 operates in the following manner.

1. A CT scan of the patient (i.e., a CT scan of the patient's bone which is to be cut) is loaded on the surgeon's computer (e.g., at his/her office) which is running appropriate pre-plan software, i.e., pre-operative surgical planning software (e.g., the Orthodoc® pre-plan software).

2. The computer uses the CT scan of the patient to generate a virtual model of the patient's bone.

3. The surgeon uses the pre-plan software (i.e., the pre-operative surgical planning software) to determine the desired shape of the bone after cutting, i.e., by overlaying a virtual model of the desired implant on the virtual model of the patient's bone.

4. A computer file containing this pre-plan information is sent to novel surgical robot system 5 prior to the surgical procedure.

5. In the operating room, the surgeon uses digitizer 25 to digitize a plurality of points on the patient's actual bone and, using this information, novel surgical robot system 5 determines the location of the patient's bone with respect to the surgical robot. In other words, the location of the bone which is to be cut is determined in terms of the coordinate system of the surgical robot.

6. The coordinate system of the pre-plan file is placed into proper registration with the coordinate system of the surgical robot so that the cut locations in the pre-plan file are properly registered in the coordinate system of the surgical robot. This action also synchronizes the angle of view of the CT image in the pre-plan file with the angle of view of the image captured by video camera 30.

7. Thereafter, the position of the bone with respect to the surgical robot is either fixed (e.g., by clamping the bone and the surgical robot to one another) or monitored by spatial sensors (e.g., so that any changes in position of the bone vis-à-vis the surgical robot can be compensated for).

8. The screen 35 displayed to the surgeon preferably comprises multiple images:
   a. the slice image of the bone from the CT scan, including pre-plan markings;
   b. the virtual model of the bone which was generated from the CT image (sometimes hereinafter referred to as the "3D view"); and
   c. the actual image of the bone and the surgical cutter provided by video camera 30.

Preferably all of these images (i.e., the CT slice image, the virtual model image and the video camera image of the bone and the surgical cutter) are shown from the same angle of view where appropriate. Additional images (e.g., other CT slice images) may also be provided on screen 35.

9. When the surgeon is ready, novel surgical robot system 5 commences automatic cutting of the bone according to the instructions contained in the pre-plan file.

10. If, at some point during the surgical procedure, the surgeon wishes to take manual control of the surgical robot, the surgeon can stop the surgical robot and thereafter manually direct cutting by the surgical robot. However, before manual cutting can commence, the surgeon is required to set some boundaries for the manual cutting. This is done using the workstation provided on the novel surgical robot system 5, including the standard input devices associated with the workstation such as a keyboard, a mouse, a joystick, etc. The workstation display 35 also shows these manual cutting boundaries on the screen, preferably using a different color to distinguish the manual cut boundaries from the pre-planned cut. As noted above, these manual cutting boundaries include, but are not limited to, the maximum depth of the manual cutting (i.e., movement along the Z axis), as well as the maximum longitudinal and lateral movements of the manual cutting (i.e., movement along the X and Y axes). The surgeon can then make the manual cut by physical command (e.g., under joystick control) or by computer command (e.g., by selecting a predetermined manual cut from a drop-down menu of manual cuts, e.g., "cut a trough" of diameter A, length B, at depth C). For clarity of description, this disclosure will hereinafter be discussed in the context of joystick control, although it should be appreciated that it is equally applicable to cutting by computer command.

Figure 4:
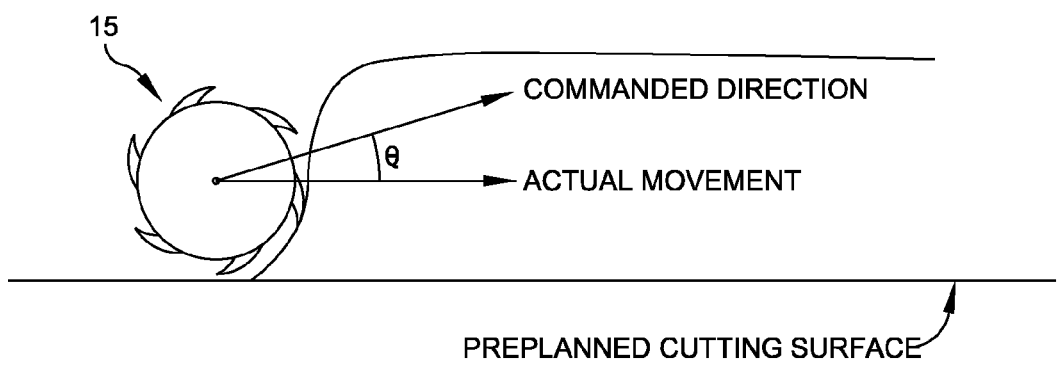
FIG. 4 is a schematic view showing how the novel surgical robot system of FIGS. 1-3 can modify joystick commands so as to improve the actual movement of the cutter.

11. When the surgeon is ready to take manual control of the surgical robot using the joystick, the surgeon activates the joystick by pressing the button on the joystick which activates the joystick and then the surgeon uses the joystick to manually direct the surgical cutter in the desired direction. During such physical control of the cutter, the surgeon can turn the high speed milling cutter on/off using the cutter switch 45. During manual movement of the cutter, the motion of the surgical robot is preferably controlled according to the following rules:
   (a) if the cutter is turned off and the cutter is out of the bone, then the surgical robot moves the according to the surgeon commands provided by the joystick;
   (b) if the cutter is on and the cutter is inside the bone, then the cutter moves according to the surgeon commands provided by the joystick, but cannot go beyond the predefined volume established by the manual cutting boundaries, and the feed rate of the cutter is limited by the software so that cutting is performed smoothly;
   (c) if the cutter is on and the cutter is inside the bone, and if there is no command from the surgeon via the joystick, then the surgical robot gradually removes the bone around the current position of the cutter according to the surgical pre-plan; and
   (d) if the cutter is on and the cutter is near to the surface of the cutting volume established by the manual cutting boundaries, then the movement of the cutter is "snapped" to the cutting surface established by the manual cutting boundaries and the cutter moves in alignment with the manual cutting boundaries (see FIG. 4, which shows that if the angle between the commanded direction is smaller than a certain amount, the actual movement of the cutter is adjusted to be parallel with the pre-planned cutting surface).

Various modifications may be made to the novel surgical robot system described above without departing from the scope of the present invention.

By way of example but not limitation, a surgical robot with fewer than 5 axes, or with more than 5 axes, may be used (e.g., the surgical robot may comprise a 4-axis device, a 6-axis device, a 7-axis device, etc.).

By way of further example but not limitation, cutting devices other than a high speed milling burr may be used, e.g., the novel surgical robot system may use an oscillating saw, a waterjet, an ablation laser and/or another tool which can cut or remove bone.

Figure 5A:
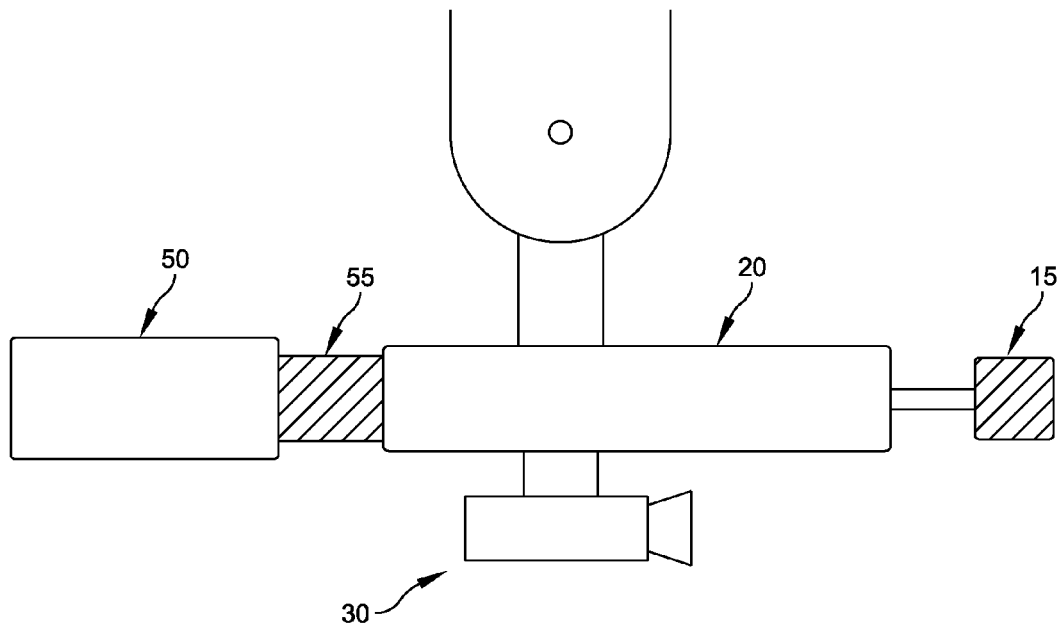
FIGS. 5A and 5B are schematic views showing how a force sensor command can be used to control actual movement of the cutter.
Figure 5B:
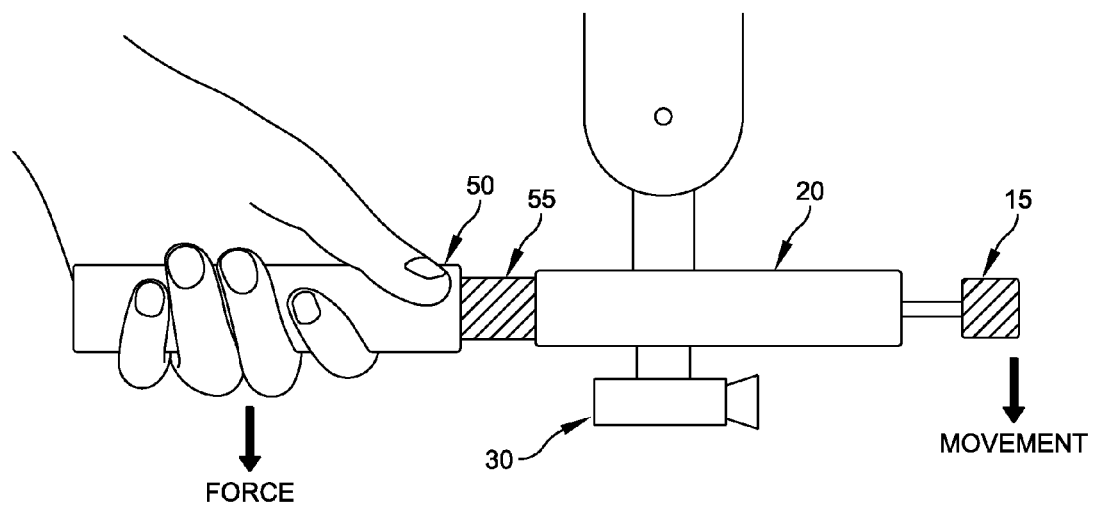

It is also anticipated that the surgeon can use other user controls in place of a joystick, e.g., a handle 50 with a 6-axis force sensor 55 can be attached to the robot end effector 20 (FIG. 5A), with the surgeon manually controlling the disposition of the cutter 15 by moving the handle 50 which is monitored by the force sensor 55 (FIG. 5B).

Furthermore, the manual on/off cutter switch 45 can be replaced by an "automatic cutter switch" which turns the cutter on whenever the cutter approaches within a predefined distance of unremoved bone.

Instead of the digitizer 25, robot 10 can use other position sensing devices (e.g., infra-red trackers, magnetic digitizers, etc.) to determine the location of the bone.

Thus it will be seen that, with the present invention, the surgeon can manually command the direction of cutter movement, but cutting can commence only after the surgeon establishes manual cutting boundaries, and the feed rate of the cutting is controlled by the software. Furthermore, the system software recognizes the volume of the bone, the volume of the removed bone and volume of the bone which should be removed, and adaptively controls the robot to appropriately shape the bone. And, at the surface of the cutting volume, the movement of the robot snaps to the surface.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for cutting bone, the method comprising:
providing pre-planned cutting instructions to a surgical robot;
automatically cutting bone with the surgical robot using the pre-planned cutting instructions;
enabling a surgeon to assert manual control of the surgical robot at any time while the surgical robot is automatically cutting bone according to the pre-planned cutting instructions, by: (i) interrupting automatic operation of the surgical robot; (ii) establishing manual cutting boundaries to limit cutting by the surgical robot while the surgical robot is under the manual control of the surgeon; and (iii) manually controlling cutting by the surgical robot using input controls on the surgical robot;
wherein the surgical robot comprises an end effector;
wherein the cutter is attached to the end effector;
wherein the method further comprises providing:
position determining means for determining the position of a bone which is to be cut vis-à-vis the surgical robot;
pre-plan means for storing the pre-planned cutting instructions and instructing the surgical robot to cut bone in accordance with the same;
a display for displaying the pre-planned cutting instructions; and
a video camera attached to the surgical robot for capturing an image of a working portion of the cutter, wherein the display displays the pre-planned cutting instructions and the image captured by the video camera.

2. A method according to claim 1 wherein the surgical robot controls the feed rate of the cutter even when the surgeon is asserting manual control of the surgical robot.

3. A method according to claim 1 wherein the surgical robot asserts control of the cutter when the cutter approaches the manual cutting boundaries while under manual control of the surgeon.

4. The method according to claim 1 wherein the input controls require the surgeon to input the manual cutting boundaries before manual control of the cutter is enabled.

5. A surgical robot system according to claim 4 wherein the surgical robot controls the feed rate of the cutter even when manual control of the cutter is enabled.

6. The method according to claim 1 wherein the manual cutting boundaries comprise a maximum longitudinal movement, a maximum lateral movement and a maximum depth.

7. The method according to claim 1 wherein the pre-planned cutting instructions and the image captured by the video camera are synchronized to the same angle of view.

8. The method according to claim 1 wherein, even when manual control of the cutter is established, the surgical robot is controlled by the following rules:
(a) if the cutter is turned off and the cutter is out of the bone, then the surgical robot moves the cutter according to the surgeon commands provided by the input controls;
(b) if the cutter is on and the cutter is inside the bone, then the cutter moves according to the surgeon commands provided by the input controls, but cannot go beyond the predefined volume established by the manual cutting boundaries, and the feed rate of the cutter is limited by the software so that cutting is performed smoothly;
(c) if the cutter is on and the cutter is inside the bone, and if there is no command from the surgeon via the input controls, then the surgical robot gradually removes the bone around the current position of the cutter according to the pre-planned cutting instructions; and
(d) if the cutter is on and the cutter is near to the surface of the cutting volume established by the manual cutting boundaries, then the movement of the cutter is snapped to the cutting surface established by the manual cutting boundaries and the cutter moves in alignment with the manual cutting boundaries.

9. The method according to claim 1 wherein the input controls comprise a joystick.

10. The method according to claim 1 wherein the input controls comprise a keyboard.

11. The method according to claim 1 wherein the method further comprises providing a digitizer for determining the position of a bone which is to be cut vis-à-vis the surgical robot.

12. The method according to claim 1 wherein the cutter comprises a high speed milling burr.

13. The method according to claim 1 wherein the cutter comprises an oscillating saw.

14. The method according to claim 1 wherein the cutter comprises a waterjet.

15. The method according to claim 1 wherein the cutter comprises an ablation laser.

16. The method according to claim 1 wherein the method further comprises providing infra-red trackers for determining the position of a bone which is to be cut vis-à-vis the surgical robot.

17. The method according to claim 1 wherein the method further comprises providing a magnetic digitizer for determining the position of a bone which is to be cut vis-à-vis the surgical robot.

18. A method for cutting bone, the method comprising:
providing pre-planned cutting instructions to a surgical robot;
automatically cutting bone with the surgical robot using the pre-planned cutting instructions;
enabling a surgeon to assert manual control of the surgical robot at any time while the surgical robot is automatically cutting bone according to the pre-planned cutting instructions, by: (i) interrupting automatic operation of the surgical robot; (ii) establishing manual cutting boundaries to limit cutting by the surgical robot while the surgical robot is under the manual control of the surgeon; and (iii) manually controlling cutting by the surgical robot using input controls on the surgical robot;
wherein, even when manual control of the cutter is established, the surgical robot is controlled by the following rules:
(a) if the cutter is turned off and the cutter is out of the bone, then the surgical robot moves the cutter according to the surgeon commands provided by the input controls;
(b) if the cutter is on and the cutter is inside the bone, then the cutter moves according to the surgeon commands provided by the input controls, but cannot go beyond the predefined volume established by the manual cutting boundaries, and the feed rate of the cutter is limited by the software so that cutting is performed smoothly;

(c) if the cutter is on and the cutter is inside the bone, and if there is no command from the surgeon via the input controls, then the surgical robot gradually removes the bone around the current position of the cutter according to the pre-planned cutting instructions; and
(d) if the cutter is on and the cutter is near to the surface of the cutting volume established by the manual cutting boundaries, then the movement of the cutter is snapped to the cutting surface established by the manual cutting boundaries and the cutter moves in alignment with the manual cutting boundaries.

19. A method for cutting bone, the method comprising:

providing pre-planned cutting instructions to a surgical robot;

automatically cutting bone with the surgical robot using the pre-planned cutting instructions;

enabling a surgeon to assert manual control of the surgical robot at any time while the surgical robot is automatically cutting bone according to the pre-planned cutting instructions, by: (i) interrupting automatic operation of the surgical robot;

(ii) establishing manual cutting boundaries to limit cutting by the surgical robot while the surgical robot is under the manual control of the surgeon; and (iii) manually controlling cutting by the surgical robot using input controls on the surgical robot; and wherein if the cutter is on and the cutter is near to the surface of the cutting volume established by the manual cutting boundaries, then the movement of the cutter is snapped to the cutting surface established by the manual cutting boundaries and the cutter moves in alignment with the manual cutting boundaries.

* * * * *